(12) United States Patent
Wu et al.

(10) Patent No.: US 7,879,005 B2
(45) Date of Patent: *Feb. 1, 2011

(54) DEVICE AND METHOD FOR COLLAPSING AN ANGIOPLASTY BALLOON

(75) Inventors: Show-Mean Wu, San Diego, CA (US); Herbert R. Radisch, Jr., San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 944 days.

This patent is subject to a terminal disclaimer.

(21) Appl. No.: 11/716,281

(22) Filed: Mar. 9, 2007

(65) Prior Publication Data

US 2007/0156166 A1    Jul. 5, 2007

Related U.S. Application Data

(63) Continuation of application No. 10/367,143, filed on Feb. 13, 2003, now Pat. No. 7,285,109.

(51) Int. Cl.
*A61M 29/00* (2006.01)

(52) U.S. Cl. .................................. 604/103.03

(58) Field of Classification Search ......... 606/191–194; 623/1.11–1.12; 604/96.01–9.017, 103.01–103.09
See application file for complete search history.

(56) References Cited

U.S. PATENT DOCUMENTS

| | | | |
|---|---|---|---|
| 4,140,126 A | 2/1979 | Choudhury | 128/325 |
| 4,141,364 A | 2/1979 | Schultze | 128/349 |
| 4,263,236 A | 4/1981 | Briggs et al. | 264/26 |
| 4,292,974 A | 10/1981 | Fogarty et al. | 128/344 |
| 4,406,656 A | 9/1983 | Hattler et al. | 604/280 |
| 4,444,186 A | 4/1984 | Wolvek et al. | 128/325 |
| 4,456,000 A | 6/1984 | Schjeldahl et al. | 128/1 |
| 4,608,984 A | 9/1986 | Fogarty | 128/344 |
| 4,627,436 A | 12/1986 | Leckrone | 128/303.1 |
| 4,685,458 A | 8/1987 | Leckrone | 128/303.1 |
| 4,686,982 A | 8/1987 | Nash | 128/305 |
| 4,705,517 A | 11/1987 | DiPisa, Jr. | 623/12 |
| 4,710,181 A | 12/1987 | Fuqua | 604/280 |
| 4,723,549 A | 2/1988 | Wholey et al. | 128/344 |
| 4,738,666 A | 4/1988 | Fuqua | 604/280 |
| 4,784,636 A | 11/1988 | Rydell | 604/22 |
| 4,787,388 A | 11/1988 | Hofmann | 128/344 |
| 4,832,691 A | 5/1989 | Witzel | 604/96 |

(Continued)

OTHER PUBLICATIONS

U.S. Appl. No. 10/367,143, filed Feb. 13, 2003, Wu et al.

(Continued)

*Primary Examiner*—Kevin T Truong
(74) *Attorney, Agent, or Firm*—Vidas, Arrett & Steinkaus, P.A.

(57) ABSTRACT

A device for collapsing a balloon in the vasculature of a patient after an angioplasty procedure includes a balloon and at least one elastomeric member that is attached to the inner surface of the balloon at a plurality of attachment points. Preferably, the elastomeric member is an annular band that will stretch during balloon inflation. Consequently, when the balloon is deflated, the elastomeric member pulls on the balloon at its attachment points to return the balloon to a predetermined configuration, wherein the balloon collapses inwardly onto itself for subsequent removal of the balloon from the vessel.

21 Claims, 1 Drawing Sheet

U.S. PATENT DOCUMENTS

| | | | | |
|---|---|---|---|---|
| RE32,983 | E | 7/1989 | Levy | |
| 4,896,669 | A | 1/1990 | Bhate et al. | 606/194 |
| 4,896,670 | A | 1/1990 | Crittenden | 606/194 |
| 5,015,231 | A | 5/1991 | Keith et al. | 604/96 |
| 5,042,985 | A | 8/1991 | Elliott et al. | 606/192 |
| 5,053,044 | A | 10/1991 | Mueller et al. | 606/159 |
| 5,059,178 | A | 10/1991 | Ya | 604/101 |
| 5,066,298 | A | 11/1991 | Hess | 606/194 |
| 5,078,725 | A | 1/1992 | Enderle et al. | 606/193 |
| 5,108,415 | A | 4/1992 | Pinchuk et al. | 606/194 |
| 5,116,318 | A | 5/1992 | Hillstead | 604/96 |
| 5,141,494 | A | 8/1992 | Danforth et al. | 604/96 |
| 5,147,302 | A | 9/1992 | Euteneuer et al. | 604/103 |
| 5,196,024 | A | 3/1993 | Barath | 606/159 |
| 5,209,799 | A | 5/1993 | Vigil | 156/156 |
| 5,221,261 | A | 6/1993 | Termin et al. | 604/104 |
| 5,226,887 | A | 7/1993 | Farr et al. | 604/96 |
| 5,273,536 | A | 12/1993 | Savas | 604/96 |
| 5,318,587 | A | 6/1994 | Davey | 606/194 |
| 5,342,301 | A * | 8/1994 | Saab | 604/103.13 |
| 5,342,307 | A | 8/1994 | Euteneuer et al. | 604/103 |
| 5,350,361 | A | 9/1994 | Tsukashima et al. | 604/96 |
| 5,372,601 | A | 12/1994 | Lary | 606/159 |
| 5,456,666 | A | 10/1995 | Campbell et al. | 604/96 |
| 5,458,572 | A | 10/1995 | Campbell et al. | 604/96 |
| 5,478,319 | A | 12/1995 | Campbell et al. | 604/96 |
| 5,490,839 | A | 2/1996 | Wang et al. | 604/96 |
| 5,556,405 | A | 9/1996 | Lary | 606/159 |
| 5,690,613 | A | 11/1997 | Verbeek | 604/103 |
| 5,783,227 | A | 7/1998 | Dunham | 425/318 |
| 5,792,172 | A | 8/1998 | Fischell et al. | 606/198 |
| 5,843,027 | A | 12/1998 | Stone et al. | 604/53 |
| 6,001,118 | A | 12/1999 | Daniel et al. | 606/200 |
| 6,007,558 | A | 12/1999 | Ravenscroft et al. | 606/200 |
| 6,013,055 | A | 1/2000 | Bampos et al. | 604/96 |
| 6,013,092 | A | 1/2000 | Dehdashtian et al. | 606/194 |
| 6,126,652 | A | 10/2000 | McLeod et al. | 606/1 |
| 6,224,625 | B1 | 5/2001 | Jayaraman | 623/1.15 |
| 6,296,665 | B1 | 10/2001 | Gaudoin et al. | 606/194 |
| 6,425,882 | B1 | 7/2002 | Vigil | 604/99.01 |
| 6,428,568 | B2 | 8/2002 | Gaudoin et al. | 623/1.11 |
| 6,491,711 | B1 | 12/2002 | Durcan | 606/194 |
| 7,285,109 | B2 * | 10/2007 | Wu et al. | 604/103.03 |

OTHER PUBLICATIONS http://en.wikipedia.org/wiki/Elastomer, Mar. 15, 2010.

* cited by examiner

DEVICE AND METHOD FOR COLLAPSING AN ANGIOPLASTY BALLOON

CROSS-REFERENCE TO RELATED APPLICATIONS

This Application claims priority to and is a continuation of U.S. patent application Ser. No. 10/367,143, filed Feb. 13, 2003, now U.S. Pat. No. 7,285,109, the entire contents of which is hereby incorporated herein by reference.

FIELD OF THE INVENTION

The present invention pertains generally to balloon devices which are used in interventional medical procedures. More particularly, the present invention pertains to angioplasty balloon devices which collapse a balloon during deflation for subsequent removal from the vasculature of a patient. The present invention particularly, though not exclusively, pertains to elastomeric members which are incorporated to collapse the balloon in a uniform and predictable manner during a balloon deflation.

BACKGROUND OF THE INVENTION

Many modern surgical techniques have been developed which are employed to alleviate or obviate the stenoses that are formed when plaque builds up in a patient's vessels. For example, several balloon angioplasty devices have been proposed for insertion into a vessel to compress the stenosis and widen the passageway through the vessel. In several respects, balloon angioplasty devices afford numerous advantages over alternative methods. Foremost among these advantages is that open-heart bypass surgery can often be avoided by using angioplasty surgical techniques to relieve stenoses in the vessels that supply blood to the heart. For obvious reasons, it is preferable to avoid open heart surgery whenever possible, because such surgery, as is well known, is invasive and can consequently require significant post-operative recovery time. Accordingly, rather than many alternative procedures, it is often preferable to use relatively simpler angioplasty surgical procedures, when such procedures are feasible. Importantly, angioplasty procedures can be performed in the peripheral vessels of a patient, as well as in the vessels that supply blood to the heart.

In an angioplasty surgical procedure, the balloon of a balloon catheter is initially in a deflated configuration as it is advanced through the vasculature into a vessel and positioned next to the stenosis that is to be treated. Once the balloon has been properly positioned, fluid is infused into the balloon to expand the balloon. As the balloon expands, it dilates the stenosis in the lumen of the vessel and compresses the plaque. This causes the plaque to break up or flatten out against the vessel wall. Once the stenosis has been compressed, however, the balloon needs to be deflated. In its deflated configuration, it is then either withdrawn from the vessel or placed across another stenosis, as necessary, to restore normal blood flow through the vessel.

During the deflation of a balloon, after an angioplasty procedure and prior to its removal from the vessel, it is desirable that the balloon be deflated into a predictable configuration as evenly and as compactly as practicable to facilitate removal of the balloon through tortuous passageways of the vessel. Several polymers which are desirable for use in balloon angioplasty catheters, because of their strength, such as polyethylene terephthalate and polyethylene naphthalate, are well known for poor refold characteristics.

In light of the above, it is an object of the present invention to provide a device that is useful for collapsing a balloon into a compact pleated cross-sectional configuration during balloon deflation to facilitate removal of the balloon from a patient's body. Another object of the present invention is to provide a device that is useful for collapsing a balloon in a uniform and predictable manner during balloon deflation. Yet another object of the present invention is to provide a device which is relatively simple to manufacture, easy to use, and comparatively cost effective.

SUMMARY OF THE INVENTION

The present invention is a device for predictably collapsing a balloon into a desired reconfiguration during its deflation. For the present invention, the device includes the balloon and at least one elastomeric member that is attached to the inside surface of the balloon at predetermined attachment points. The balloon, defining a longitudinal axis, can be any angioplasty balloon known in the art. The device is particularly effective, however, in construction with balloon materials which, due to their polymeric structure, resist heat setting and exhibit poor refold.

As contemplated for the present invention, it is preferable that a plurality of elastomeric members be attached to the inner surface of the balloon to influence deflation of the balloon. In particular, each elastomeric member is a generally annular-shaped band having an unstretched diameter, $D_m$. Further, each elastomeric band is attached to the inner surface of the balloon at a plurality of attachment points and is centered on the axis of the balloon. For example, each elastomeric member can be attached to the inner surface of the balloon at multiple separate attachment points by any means well known in the art, such as by gluing, bonding with anaerobic adhesive, heat bonding and laser welding.

When more than one elastomeric members are used for the present invention, the individual elastomeric members can be positioned at predetermined distances along the axis of the balloon. The consequence of this is that the attachments points of each elastomeric member are positioned in respective planes that are perpendicular to the axis of the balloon and substantially parallel to each other. Thus, corresponding attachment points on respective elastomeric members are spaced apart from each other. Preferably, these attachment points are aligned with each other and located at predetermined distances from each other in an axial direction. The predetermined distance between each elastomeric, member may vary depending upon the particular need. Also, the attachment points need not be axially aligned and, instead, can be helically aligned along the length of the balloon axis.

In operation, the initially deflated balloon is positioned in a vessel of the patient and is then infused with fluid to perform an angioplasty procedure. In this surgical procedure, the inflating balloon may pull on the unstressed elastomeric members at the respective attachment points. During balloon inflation, the elastomeric members may stretch and expand away from the axis. Because of the elastic nature of the elastomeric members, however, each elastomeric member is biased in its stressed configuration to return to its unstressed configuration. Thus, once the fluid begins to be removed from the balloon, the elastomeric members may pull on the balloon at their respective attachment points. Since corresponding attachment points on respective elastomeric members are axially aligned with each other, this pulling action on the balloon at these corresponding attachment points may create fold lines in the axial direction. As a result, the deflating balloon may fold onto itself along the axis to form a pleated cross-sectional shape. Once the balloon is deflated and the elastomeric members have returned to their unstressed, substantially ring-shaped form, the balloon catheter may then be removed from the vessel.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
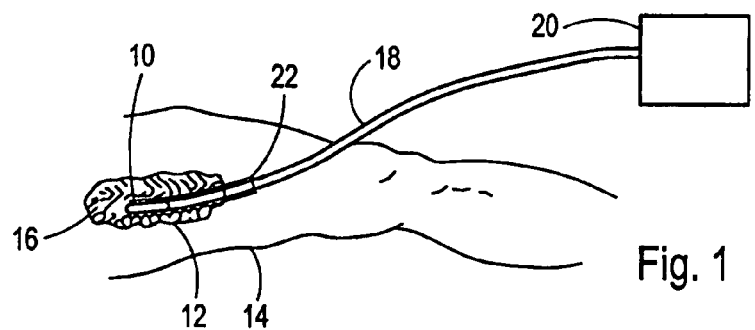
FIG. 1 is a perspective view of the present invention, shown positioned in the vasculature of a patient, with the balloon in its deflated configuration.

Referring initially to FIG. 1, an angioplasty balloon in accordance with this present invention is shown and is generally designated 10. The balloon 10 is shown inserted into a vessel 12 of a patient 14 and positioned adjacent to a stenosis 16 in the vessel 12. As is also shown, balloon 10 is connected in fluid communication with a hollow catheter tube 18 which, in turn, is connected in fluid communication with a fluid source 20. If required, the balloon 10, along with the catheter tube 18, can be inserted into the patient 14 through an insertion catheter 22. The balloon 10 is preferably made of any suitable angioplasty balloon material, such as polyethylene terephthalate or polyethylene naphthalate.

Figure 2A:
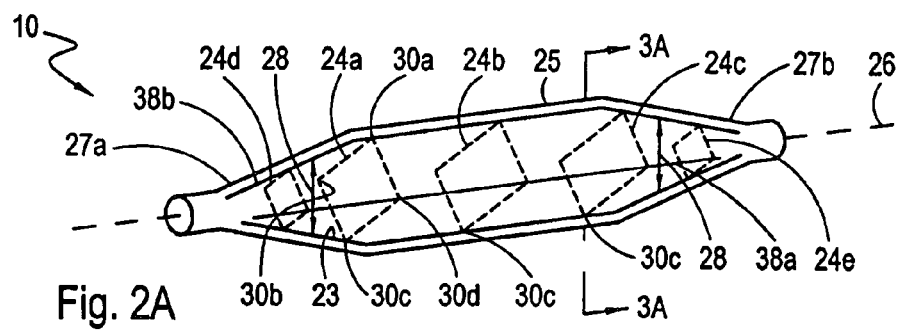
FIG. 2A is a perspective view of the present invention, when the balloon is inflated, and the elastomeric members, shown in phantom, are in their stressed configurations.
Figure 2B:
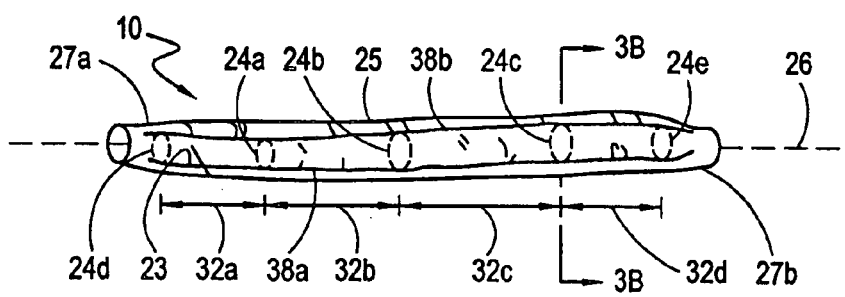
FIG. 2B is a perspective view of the present invention, when the balloon is deflated, and the elastomeric members, shown in phantom, are in their unstressed configurations.

The present invention can perhaps be best appreciated by cross-referencing FIGS. 2A and 2B. In contrast to each other, FIG. 2A shows elastomeric members 24a-e in their stressed configurations, with balloon 10 inflated. FIG. 2B, on the other hand, shows elastomeric members 24a-e in their unstressed configuration, with balloon 10 deflated. As shown in FIGS. 2A and 2B, the elastomeric members 24a-e are attached to an inner surface 23 of the balloon 10. In detail, the balloon 10 has a midsection 25 defining a longitudinal axis 26 and end portions 27a and 27b that are attached to the midsection 25. When balloon 10 is inflated (FIG. 2A), the midsection 25 of the balloon 10 is substantially cylindrical-shaped and the ends 27a-b are substantially conical-shaped. Specifically, when inflated, the ends 27a-b have a diameter 28 that decreases in a direction away from the midsection 25. FIGS. 2A and 2B show the balloon 10 with five elastomeric members 24a-e attached to the inner surface 23 of the balloon 10. In particular, two respective elastomeric members 24d-e are shown in the corresponding conical-shaped end portions 27a-b. It is to be appreciated that these five elastomeric members 24a-e are only exemplary, for there may be either fewer or more elastomeric members 24 attached to the balloon 10 as desired.

As shown in FIGS. 2A and 2B, each elastomeric member 24a-e, is positioned around the axis 26, and is attached to the inner surface 23 of the balloon 10 at a plurality of attachment points 30a-d. As shown, each elastomeric member 24a-e is attached to the inner surface 23 of the balloon 10 at four attachment points 30a-d, by any means well known in the art. These four attachment points 30a-d, however, are only exemplary. It would be appreciated that each elastomeric member 24 may be attached to the inner surface 23 of the balloon 10 at either fewer or more attachment points 30 as desired. It can also be appreciated that the attachments could be made asymmetrically or from an asymmetric folded balloon shape, if desired. In any case, these attachment points 30a-d between one of the elastomeric members 24 and the balloon 10 can perhaps be best seen in FIGS. 3A and 3B.

Figure 3A:
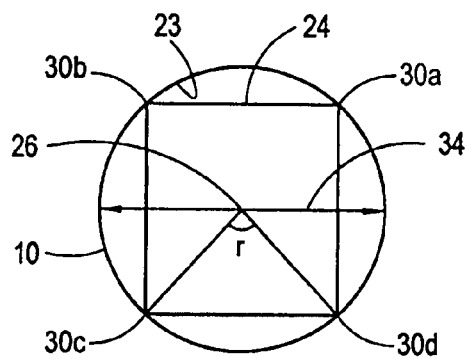
FIG. 3A is a cross-sectional view of the elastomeric member attached to the balloon as seen along the lines 3A-3A in FIG. 2A.
Figure 3B:
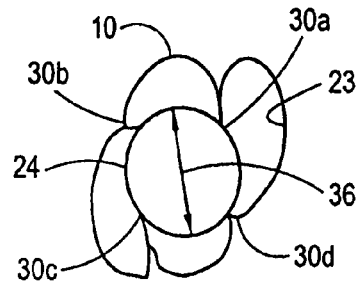
FIG. 3B is a cross-section view of the elastomeric member attached to the balloon, with the balloon in its deflated configuration as would be seen along the lines 3B-3B in FIG. 2B.

As shown in FIGS. 3A and 3B, the elastomeric member 24 is attached to the inner surface 23 of the balloon 10 at four attachment points 30a-d. With four attachment points 30a-d, each attachment point 30 is azimuthally distanced from adjacent attachment points 30 by approximately ninety degrees (90°). FIG. 3A shows an azimuthal angle, $\beta$, between attachment points 30c and 30d that is approximately ninety degrees (90°). On the other hand, when an elastomeric member 24 is attached to the balloon 10 at three attachment points 30 (not shown), each attachment point 30 is azimuthally distanced from adjacent attachment points 30 by approximately one hundred twenty degrees (120°).

Referring back to FIGS. 2A and 2B, each elastomeric member 24a-e is shown attached to the balloon 10 at its respective attachment points 30a-d. In order for the elastomeric members 24a-e to act in concert to collapse the balloon 10 during balloon deflation, it is preferable that corresponding attachment points 30a-d on respective elastomeric members 24a-e, as shown in FIG. 2A, are spaced apart from each other and are axially aligned at a predetermined linear distance 32a-d in the axial direction, as shown in FIG. 2B. For the present invention, these predetermined distances 32a-d between elastomeric members 24a-e may vary depending upon the particular need.

For the present invention, each elastomeric member 24 will move between a stressed configuration, as shown in FIGS. 2A and 3A, and an unstressed configuration, as shown in FIGS. 2B and 3B, depending on whether balloon 10 is inflated or deflated. Specifically, when balloon 10 is inflated, and when the elastomeric members 24a-e are in their stressed configurations (FIGS. 2A and 3A), balloon 10 will pull on the elastomeric members 24a-e at their respective attachment points 30a-d. As a result, when attached at four attachment points 30a-d, each elastomeric member 24 expands and assumes a substantially square or rectangular shape. This can be seen in FIGS. 2A and 3A. The inflated balloon 10 has a substantially circular cross-sectional shape with a diameter 34 ($D_b$), as shown in FIG. 3A. Furthermore, when the balloon 10 is inflated, the diameter 34 ($D_b$) of the inflated balloon 10, as shown in FIG. 3A, is greater than the diameter 36 ($D_m$) of the unstressed elastomeric member 24, as shown in FIG. 3B. More specifically, the diameter 34 of the inflated balloon 10 is approximately eight to twelve times greater than the diameter 36 of the elastomeric member 24 in its unstressed configuration. For example, the diameter 34 of the inflated balloon 10 can be ten times greater than the diameter 36 of the elastomeric member 24 ($D_b=10D_m$).

When balloon 10 is deflated, and the elastomeric members 24a-e return to their unstressed configurations (FIGS. 2B and 3B), each elastomeric member 24 may be substantially ring-shaped and may have an unstretched diameter 36, $D_m$, as shown in FIG. 3B. Each elastomeric member 24 may pull on the balloon 10 at its respective attachment points 30*a-d* to return the elastomeric member 24 to its unstressed configuration. Further, when the elastomeric members 24*a-e* pull at their respective attachment points 30*a-d*, the balloon 10 may fold over at the attachment points 30*a-d* and collapse onto itself. As a result, the balloon 10, in its deflated configuration, has a pleated cross-sectional shape, as shown in FIG. 3B.

Since corresponding attachment points 30*a-d* are axially aligned with each other, as shown in FIG. 2A, as the elastomeric members 24*a-e* pull the balloon 10 toward the axis 26, the balloon 10 may fold at fold lines 38 created by the axially aligned attachment points 30. (The fold lines 38*a* and 38*b* shown in FIGS. 2A and 2B are only exemplary.) As shown, these fold lines 38 are, preferably, oriented substantially parallel to the axis 26. Alternatively, the fold lines 38 could have a helical orientation in relation to the axis 26. In either case, these fold lines 38 assist the balloon 10 in predictably collapsing onto the axis 26, and into a desired reconfiguration after deflation.

OPERATION

In the operation of the present invention, balloon 10 is first in a deflated configuration, as shown in FIG. 2B. As shown, when the balloon 10 is deflated, the elastomeric members 24*a-e* are in their unstressed configurations. Deflated balloon 10 can then be inserted through the insertion catheter 22 and advanced into the patient 14 until the balloon 10 is positioned adjacent the stenosis 16, as seen in FIG. 1. Fluid from fluid source 20 can then be infused into balloon 10 through catheter tube 18 to inflate the balloon 10 in accordance with appropriate angioplasty procedures.

Balloon 10, when it is infused with fluid from fluid source 20, presses against the stenosis 16 to expand the lumen of the patient 14. Meanwhile, as the balloon 10 is being inflated, the elastomeric members 24*a-e* are being pulled by the inflating balloon 10 at their respective attachment points 30*a-d*. Consequently, each elastomeric member 24 moves from its unstressed configuration to its stressed configuration. In more detail, each elastomeric member 24 expands away to assume a substantially square or rectangular shape, when attached to the balloon 10 at four attachment points 30*a-d*.

In the stressed configuration, each elastomeric member 24 is biased toward its unstressed configuration to collapse the balloon 10 inwardly toward axis 26. Accordingly, when fluid is withdrawn from balloon 10, each elastomeric member 24 pulls the balloon 10 at its respective attachment points 30*a-d* to return balloon 10 to its deflated configuration, as shown in FIGS. 2B and 3B. In more detail, since corresponding attachment points 30*a-d* on respective elastomeric members 24*a-e* are axially aligned at predetermined distances 32*a-d* in the axial direction, the elastomeric members 24*a-e* pull at their respective attachment points 30*a-d* and create fold lines 38 on the balloon 10 where the balloon 10 folds over. The fold lines 38 are initially created, in large part, as a result of the elastomeric members 24*d* and 24*e* pulling on respective attachment points 30*a-d* in respective end portions 27*a* and 27*b*. As a result of the elastomeric members 24*a-e* pulling on the attachment points 30*a-d*, the balloon 10 will collapse at the fold lines 38 onto itself and fold onto the axis 26. In its deflated configuration, balloon 10 may be subsequently removed from the vessel 12 of the patient 14.

Although the present invention has been described above in accordance with an angioplasty procedure performed in the vessel 12 of a patient 14, it will be appreciated that the balloon 10 can be inserted into the vessel 12 of the patient 14 to perform a different surgical procedure. For example, the balloon 10 can be inserted into an air passageway of the patient 14 to widen the passageway. Accordingly, the present invention is intended to have universal application in surgical procedures performed on the patient 14.

While the particular Device and Method for Collapsing an Angioplasty Balloon as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A reconfiguration device which comprises:
    an elongated balloon defining an axis and having an inner surface, said balloon being moveable between an inflated configuration and a deflated configuration; and
    at least one elastomeric member attached to a plurality of attachment points on said inner surface of said balloon.

2. A device as recited in claim 1 wherein said elastomeric member is attached to said inner surface of said balloon at three or more attachment points.

3. A device as recited in claim 1 further comprising a plurality of said elastomeric members.

4. A device as recited in claim 1 wherein said elastomeric member is ring-shaped in an unstressed state, and has a diameter, $D_m$, and said balloon in said inflated configuration has a diameter, $D_b$, wherein $D_b > D_m$.

5. A device as recited in claim 1 wherein said balloon further comprises:
    a midsection having a substantially cylindrical-shape in the inflated configuration, said midsection defining the axis;
    a proximal cone portion; and
    a distal cone portion.

6. A device as recited in claim 5 wherein said elastomeric member is a first elastomeric member and said plurality of attachment points is a first plurality of attachment points, with said first plurality of attachment points located on said inner surface of said balloon in said midsection, said device further comprising:
    a second elastomeric member attached to a second plurality of attachment points on said inner surface of said balloon in said proximal cone portion; and
    a third elastomeric member attached to a third plurality of attachment points on said inner surface of said balloon in said distal cone portion.

7. A device as recited in claim 1 wherein said balloon is made of polyethylene naphthalate.

8. A collapsible balloon which comprises:
    an elongated, hollow body member defining a longitudinal axis and having an inner surface, said body member being moveable between an inflated configuration wherein said body member has a substantially circular cross-sectional shape and a deflated configuration wherein said body member has a pleated cross-sectional shape;
    a plurality of predetermined fold lines formed in said body member wherein said body member is collapsed onto said axis along said fold lines to form said pleated cross-sectional shape;
    a plurality of attachment points on said inner surface of said body; and
    at least one elastomeric member attached to said plurality of attachment points on said body member to guide said balloon into said deflated configuration.

9. A balloon as recited in claim 8 further comprising a plurality of elastomeric members.

10. A balloon as recited in claim 9 wherein each said elastomeric member is attached to said inner surface of said body member at three or more respective attachment points.

11. A balloon as recited in claim 10 wherein each said elastomeric member is ring-shaped in an unstressed state when said body member is in said deflated configuration, and further wherein each said elastomeric member is substantially polygon-shaped in a stressed state when said body member is in said inflated configuration.

12. A balloon as recited in claim 11 wherein each said elastomeric member in said unstressed configuration has a diameter, $D_m$, and said body member in said inflated configuration has a diameter, $D_b$, and wherein $D_b$ is in a range between $1.5D_m$ and $15D_m$.

13. A balloon as recited in claim 8 wherein said body member further comprises:
   a midsection having a substantially cylindrical-shape in the inflated configuration, said midsection defining the axis;
   a proximal cone portion; and
   a distal cone portion.

14. A balloon as recited in claim 13 wherein said elastomeric member is a first elastomeric member and said plurality of attachment points is a first plurality of attachment points, with said first plurality of attachment points located on said inner surface of said body member in said midsection, said balloon further comprising:
   a second elastomeric member attached to a second plurality of attachment points on said inner surface of said body member in said proximal cone portion; and
   a third elastomeric member attached to a third plurality of attachment points on said inner surface of said body member in said distal cone portion.

15. A balloon as recited in claim 8 wherein said attachment points are located on said predetermined fold lines.

16. A catheter balloon comprising:
   an inflatable body having an inner surface, the inflatable body defining a longitudinal axis; and
   an elastomeric member oriented within said inflatable body, said elastomeric member attached to said inner surface at a plurality of attachment points.

17. The catheter balloon of claim 16, wherein said elastomeric member comprises a first elastomeric member and said plurality of attachment points comprises a plurality of first attachment points, the catheter balloon further comprising:
   a second elastomeric member oriented within said inflatable body, the second elastomeric member attached to said inner surface at a plurality of second attachment points.

18. The catheter balloon of claim 17, wherein a first attachment point is aligned with a second attachment point in a direction parallel to said longitudinal axis.

19. The catheter balloon of claim 17, wherein each first attachment point is aligned with a second attachment point in a direction parallel to said longitudinal axis.

20. The catheter balloon of claim 17, said inflatable body comprising a plurality of predetermined fold lines, each predetermined fold line spanning between a first attachment point and a second attachment point.

21. The catheter balloon of claim 20, wherein said predetermined fold lines are helical in relation to said longitudinal axis.

* * * * *